(12) United States Patent
Arai et al.

(10) Patent No.: US 8,691,858 B2
(45) Date of Patent: Apr. 8, 2014

(54) COMPOSITION FOR PREPARING EMULSION OR MICROEMULSION FORMULATIONS

(75) Inventors: Shigebumi Arai, Katori (JP); Tetsuo Kubota, Haribara-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/319,753

(22) PCT Filed: May 10, 2010

(86) PCT No.: PCT/JP2010/003169
§ 371 (c)(1),
(2), (4) Date: Nov. 10, 2011

(87) PCT Pub. No.: WO2010/134279
PCT Pub. Date: Nov. 25, 2010

(65) Prior Publication Data
US 2012/0053217 A1    Mar. 1, 2012

(30) Foreign Application Priority Data
May 20, 2009    (JP) ................................ 2009-121611

(51) Int. Cl.
*A61K 31/41*    (2006.01)
(52) U.S. Cl.
USPC .......................................... 514/383; 514/784
(58) Field of Classification Search
None
See application file for complete search history.

(56) References Cited

U.S. PATENT DOCUMENTS

| | | | |
|---|---|---|---|
| 6,821,992 B1 | 11/2004 | Cooke et al. | |
| 2002/0086808 A1 | 7/2002 | Nyssen et al. | |
| 2002/0115783 A1 | 8/2002 | Nyssen et al. | |
| 2004/0132621 A1 | 7/2004 | Frisch et al. | |
| 2005/0043182 A1 | 2/2005 | Douglass et al. | |
| 2006/0205600 A1* | 9/2006 | Otsubo et al. | 504/344 |
| 2008/0015168 A1* | 1/2008 | Watanabe et al. | 514/75 |
| 2010/0234232 A1* | 9/2010 | Dairiki et al. | 504/343 |

FOREIGN PATENT DOCUMENTS

| | | | |
|---|---|---|---|
| JP | 55-136201 A | 10/1980 | |
| JP | 05-112402 A | 5/1993 | |
| JP | 2002-194205 A | 7/2002 | |
| JP | 2003-506465 A | 2/2003 | |
| JP | 2006-509807 A | 3/2006 | |
| JP | 2006-199687 A | 8/2006 | |
| JP | 2007-015959 A | 1/2007 | |
| JP | 2008-308508 A | 12/2008 | |
| WO | WO 96/16544 A2 | 6/1996 | |
| WO | WO 2007/110435 A2 | 10/2007 | |
| WO | WO 2009063608 A1 * | 5/2009 | |

OTHER PUBLICATIONS

International Search Report mailed Aug. 3, 2010, in PCT/JP2010/003169, 4 pages.

* cited by examiner

*Primary Examiner* — Robert T Crow
*Assistant Examiner* — Doan Phan
(74) *Attorney, Agent, or Firm* — Foley & Lardner LLP

(57) ABSTRACT

Provided is a composition for preparing emulsion or microemulsion formulations that demonstrates favorable dilution properties without being affected by the solubilities of constituent components. The composition for preparing emulsion or microemulsion formulations contains a component (A): a polyoxyalkylene allyl phenyl ether, polyoxyalkylene aralkyl phenyl ether or polyoxyalkylene aralkenyl phenyl ether, a component (B): a polyoxyalkylene sorbitan alkylate, a component (C): a dialkylsulfosuccinate, and a component (D): an ester ether-based solvent. An emulsion or microemulsion formulation containing the composition is also provided.

13 Claims, No Drawings

COMPOSITION FOR PREPARING EMULSION OR MICROEMULSION FORMULATIONS

CROSS-REFERENCE TO RELATED APPLICATIONS

This application is a National Stage application of PCT/JP2010/003169, filed May 10, 2010, which claims priority from Japanese application JP 2009-121611, filed May 20, 2009.

TECHNICAL FIELD

The present invention relates to a composition for preparing emulsion or microemulsion formulations. More particularly, the present invention relates to a composition for preparing emulsion or microemulsion formulations that demonstrate favorable diluting properties without being affected by the solubilities of constituent components.

The present application claims priority on the basis of Japanese Patent Application No. 2009-121611 filed in Japan on May 20, 2009, the contents of which are incorporated herein by reference.

BACKGROUND ART

Known examples of the types of the forms of agricultural chemicals include: milky white formulations in the form of concentrated oil-in-water emulsions obtained by emulsifying and dispersing a water-insoluble agricultural chemical active ingredient in water in the form of fine particles by adding an emulsifier (emulsion formulations (emulsion, oil in water: EW or concentrated emulsion: CE)); and thermodynamically stable and transparent formulations obtained by mixing mutually incompatible water and oil in the manner of ordinary emulsions, but consisting of dispersed particles that are much smaller (mean particle diameter: 0.1 μm or less) than the particles of ordinary emulsions (microemulsion formulations (microemulsion: ME)).

More specifically, Patent Document 1 discloses a wood preservative having as an active ingredient thereof an anionic surfactant containing a sulfonate or laurylsulfate ester. A preservative containing a sulfosuccinate ester is described as a comparative example of a formulation in Patent Document 1.

Patent Document 2 discloses a wood preservative, ant repellent and anti-mold agent containing as an active ingredient thereof a polyoxyalkylene alkyl ether obtained by adding at least one type of compound selected from the group consisting of ethylene oxide, propylene oxide and butylene oxide to an alkyl alcohol. A preservative containing a sorbitan fatty acid ester-based surfactant and a preservative containing polyoxyethylene styrenated phenyl ether are described as comparative examples of formulations in Patent Document 2.

Patent Document 3 describes a microemulsion preparation containing: a) one or more agricultural chemical active ingredients; b) one or more non-alcoholic organic solvents; c) one or more anionic surfactants; and d) one or more nonionic surfactants.

Patent Document 4 discloses an emulsion containing a surfactant. Examples of preferable surfactants include: f1) alkoxylation product obtained by ethylene oxide alkoxylation or propylene oxide alkoxylation of a condensation product of an aromatic compound containing a phenolic OH group, formaldehyde and an NH functional group; f2) a carbonate, sulfate and phosphate of an alkaline metal or alkaline earth metal; f3) a polymer containing repeating succinyl units; f4) a non-ionically or ionically modified compound selected from the group consisting of alkoxylate, alkylolamide, ester, amine oxide and alkylpolyglycoside; f5) a reaction product of an alkylene oxide and sorbitan ester, an oxyalkylated acetylenediol and acetylene glycol, and an oxyalkylated phenol; f6) ionically or non-ionically modified polymeric surfactants selected from the group consisting of homo- and copolymers, grafts and graft copolymers, and random and linear block copolymers; f7) anionic surfactants such as ether sulfates, ether carboxylates and phosphate esters; f8) anionic surfactants such as sulfosuccinate esters, alkylbenzene sulfonates and salts of polyacrylic acid, polyethylene sulfonic acid, polystyrene sulfonic acid, polymethacrylic acid or polyphosphoric acid; and f9) lignin-based compounds, and particularly lignosulfonates.

Patent Document 5 discloses a microemulsion-formable concentrate of a hydrophobic agricultural chemical containing: (a) at least one type of hydrophobic agricultural chemical, (b) a concentrate of a first solvent selected from alkyl alkanoates, a polyvalent alcohol, a polyvalent alcohol concentration product and a mixture thereof, and (c) at least one type of surfactant. Examples of the surfactant include cationic surfactants such as polyalkoxylated aliphatic amines, nonionic surfactants such as polyalkylene oxide alkyl ethers, and anionic surfactants such as alkylbenzene sulfonates.

However, the emulsion or microemulsion formulations described in these documents may require a large amount of surfactant or emulsifier corresponding to the solubility of the active ingredient. In such cases, a large amount of foam may form during preparation of the formulation and may be difficult to remove from the formulation container. In the case of diluting the formulations, the stability of the emulsion or microemulsion may decrease. In addition, the use of a large amount of surfactant for the purpose of enhancing solubility results in increased costs.

PRIOR ART DOCUMENT

Patent Documents

[Patent Document 1] Japanese Patent Application No. Laid-Open Publication 2007-15959
[Patent Document 2] Japanese Patent Application Laid-Open Publication No. 2006-199687
[Patent Document 3] Japanese Patent Application Laid-Open Publication (Translation of PCT Application) No. 2006-509807
[Patent Document 4] Japanese Patent Application Laid-Open Publication No. 2002-194205
[Patent Document 5] Japanese Patent Application Laid-Open Publication No. 2008-308508

SUMMARY OF THE INVENTION

Problems to be Solved by the Invention

With the foregoing in view, an object of the present invention is to provide a composition for preparing emulsion or microemulsion formulations having favorable diluting properties without being affected by the solubilities of constituent components.

Means for Solving the Problems

In order to solve the aforementioned problems, the inventors of the present invention found that a favorable emulsion or microemulsion formulation demonstrating little foaming can be prepared by mixing an anionic surfactant with a certain type of combination of nonionic surfactants and further combining with a specific polar solvent therewith. The present invention was completed by conducting further studies on the basis of this finding.

Namely, the present invention includes the aspects described below.

(1) A composition for preparing emulsion or microemulsion formulations, including:
   component (A): a polyoxyalkylene allyl phenyl ether, polyoxyalkylene aralkyl phenyl ether or polyoxyalkylene aralkenyl phenyl ether;
   component (B): a polyoxyalkylene sorbitan alkylate;
   component (C): a dialkylsulfosuccinate; and
   component (D): an ester ether-based solvent.

(2) The composition for preparing emulsion or microemulsion formulations described in (1) above, wherein the ratio of the total amount of component (A) and component (B) to the amount of component (C) is within the range of 1:2 to 1:7, and
   the ratio of the amount of component (A) to the amount of component (B) is within the range of 2:1 to 1:2.

(3) The composition for preparing emulsion or microemulsion formulations described in (1) or (2) above, wherein the total amount of component (A), component (B) and component (C) is 20% by weight to 50% by weight, and the amount of component (D) is 50% by weight to 80% by weight based on a value of 100% by weight for the total amount of component (A), component (B), component (C) and component (D).

(4) The composition for preparing emulsion or microemulsion formulations described in (1) or (2) above, further including a component (E): a polar solvent other than the ester ether-based solvent.

(5) The composition for preparing emulsion or microemulsion formulations described in (4) above, wherein the total amount of component (A), component (B) and component (C) is 20% by weight to 50% by weight, the total amount of component (D) and component (E) is 50% by weight to 80% by weight, and the amount of component (E) is 10% by weight to 40% by weight based on a value of 100% by weight for the total amount of component (A), component (B), component (C), component (D) and component (E).

(6) The composition for preparing emulsion or microemulsion formulations described in any one of (1) to (5) above, further including a component (F): an agricultural chemical active ingredient.

(7) The composition for preparing emulsion or microemulsion formulations described in (6) above, including 1 to 43 parts by weight of the component (F) based on 100 parts by weight of the total amount of component (A), component (B), component (C), component (D) and component (E).

(8) An emulsion or microemulsion formulation, including:
   the composition for preparing emulsion or microemulsion formulations described in any one of (1) to (7) above.

(9) An emulsion or microemulsion formulation obtained by diluting with water the composition for preparing emulsion or microemulsion formulations described in any one of (1) to (7) above.

(10) The emulsion or microemulsion formulation described in (8) or (9) above, which is used to preserve wood.

Effects of the Invention

The composition for preparing emulsion or microemulsion formulations according to the present invention is able to provide an emulsion or microemulsion formulation that demonstrates favorable diluting properties without being affected by the solubilities of constituent components. The composition for preparing emulsion or microemulsion formulations according to the present invention permits easy handling during preparation as a result of demonstrating little foaming. Moreover, the composition for preparing emulsion or microemulsion formulations according to the present invention enables an emulsion or microemulsion to be stably maintained even if diluted with water.

DESCRIPTION OF THE EMBODIMENTS

The following provides a detailed explanation of the present invention.

1) Composition for Preparing Emulsion or Microemulsion Formulations

The composition for preparing emulsion or microemulsion formulations according to the present invention contains a component (A), a component (B), a component (C) and a component (D), and as necessary, a component (E) and/or a component (F).

[Component (A)]

The component (A) used in the composition for preparing emulsion or microemulsion formulations according to the present invention is a polyoxyalkylene allyl phenyl ether, polyoxyalkylene aralkyl phenyl ether or polyoxyalkylene aralkenyl phenyl ether.

Polyoxyalkylene allyl phenyl ethers are obtained by linking a polyoxyalkylene group and an allyl phenyl group with an ether bond. Polyoxyalkylene aralkyl phenyl ethers are obtained by linking a polyoxyalkylene group and an aralkyl phenyl group with an ether bond. Polyoxyalkylene aralkenyl phenyl ethers are obtained by linking a polyoxyalkylene group and an aralkenyl phenyl group with an ether bond.

Examples of the polyoxyalkylene group include a polyoxyethylene group, a polyoxypropylene group, a polyoxybutylene group and a polyoxyethylene-polyoxypropylene group. The degree of polymerization of the polyoxyalkylene group is normally 2 to 50, preferably 5 to 30 and more preferably 10 to 25.

The allyl phenyl group is obtained by substituting at least one allyl group in a phenyl group, the aralkyl phenyl group is obtained by substituting at least one aralkyl group in a phenyl group, and the aralkenyl phenyl group is obtained by substituting at least one aralkenyl group in a phenyl group. Specific examples of the allyl phenyl group, the aralkyl phenyl group and the aralkenyl phenyl group include a monoallyl phenyl group, a diallyl phenyl group, a triallyl phenyl group, a monobenzyl phenyl group, a dibenzyl phenyl group, a tribenzyl phenyl group, a monostyryl phenyl group, a distyryl phenyl group and a tristyryl phenyl group. A substituent such as an alkyl group may be present in an aromatic ring in the aralkyl group or aralkenyl group. In addition, examples of the aromatic ring in the aralkyl group or aralkenyl group include a benzene ring and naphthalene ring.

Specific examples of component (A) include: polyoxyethylene monoallyl phenyl ether, polyoxyethylene diallyl phenyl ether, polyoxyethylene triallyl phenyl ether, polyoxypropylene monoallyl phenyl ether, polyoxyethylene-polyoxypropylene triallyl phenyl ether; polyoxyethylene monobenzyl phenyl ether, polyoxyethylene dibenzyl phenyl ether, polyoxyethylene tribenzyl phenyl ether, polyoxypropylene tribenzyl phenyl ether, polyoxyethylene-polyoxypropylene tribenzyl phenyl ether; polyoxyethylene monostyryl phenyl ether, polyoxyethylene distyryl phenyl ether, polyoxyethylene tristyryl phenyl ether, polyoxypropylene tristyryl phenyl ether and polyoxyethylene-polyoxypropylene tristyryl phenyl ether. Among these, polyoxyethylene monoallyl phenyl ether, polyoxyethylene diallyl phenyl ether and polyoxyethylene triallyl phenyl ether are preferable. One type of the component (A) may be used alone, or two or more types may be used in combination.

[Component B]

The component (B) used in the composition for preparing emulsion or microemulsion formulations according to the present invention is a polyoxyalkylene sorbitan alkylate.

Specific examples of polyoxyalkylene sorbitan alkylates include polyoxyethylene sorbitan oleate, polyoxyethylene sorbitan stearate, polyoxyethylene sorbitan palmitate and polyoxyethylene-polyoxypropylene sorbitan dilaurate. Among these, polyoxyethylene sorbitan monooleate is preferable.

[Component C]

The component (C) used in the composition for preparing emulsion or microemulsion formulations according to the present invention is a dialkyl sulfosuccinate.

Examples of the dialkyl sulfosuccinate include dibutyl sulfosuccinate, dioctyl sulfosuccinate and dilauryl sulfosuccinate. Examples of metals used to form a salt include: alkaline metals such as sodium, potassium or lithiuml; and alkaline earth metals such as beryllium, magnesium, or calcium.

Among these dialkyl sulfosuccinates, magnesium dioctyl sulfosuccinate is preferable.

Although there are no particular limitations on the mixing ratio of the components (A) to (C), the ratio of the total amount of component (A) and component (B) to the amount of component (C) is preferably 1:2 to 7:1 and more preferably 2:1 to 4:1, and the ratio of the amount of component (A) to the amount of component (B) is preferably 2:1 to 1:2 and more preferably 3:2 to 2:3.

(Component D)

The component (D) used in the composition for preparing emulsion or microemulsion formulations according to the present invention is an ester ether-based solvent.

Specific examples of the ester ether-based solvent include methoxybutyl acetate, methyl cellosolve acetate, ethyl cellosolve acetate, butyl cellosolve acetate, methyl carbitol acetate, ethyl carbitol acetate, butyl carbitol acetate and 3-methoxy-3-methyl-1-butyl acetate. Among these, 3-methoxy-3-methyl-1-butyl acetate is preferable.

Although there are no particular limitations on the respective amounts of component (A), component (B), component (C) and component (D) in the composition for preparing emulsion or microemulsion formulations, the total amount of component (A), component (B) and component (C) is preferably 20% by weight to 50% by weight and more preferably 25% by weight to 40% by weight, and the amount of component (D) is preferably 50% by weight to 80% by weight and more preferably 60% by weight to 75% by weight, based on a value of 100% by weight for the total amount of component (A), component (B), component (C) and component (D).

[Component E]

The component (E) used as necessary in the composition for preparing emulsion or microemulsion formulations according to the present invention is a polar solvent other than the ester ether-based solvent.

The component (E) is preferable in the case of using an agricultural chemical active ingredient (component (F)) having low solubility with respect to the component (D).

Examples of the polar solvent of the component (E) include ketones, lactones, N methyl-2-pyrrolidone, n-amyl acetate, propylene glycol monomethyl ether, propylene carbonate, butyl lactate ester, ethyl lactate ester, isobornyl acetate, tetrahydrofurfuryl alcohol, 3-methoxy-3-methyl-1-butanol, sulfolane and D-limonene. One type of polar solvent maybe used alone, or two or more types may be used in combination.

Among the polar solvents of the component (E), ketones and lactones are preferable, and lactones are particularly preferable, since they allow the obtaining of a composition having further improved dispersibility.

Examples of ketones include acetone, methyl ethyl ketone, diethyl ketone, methyl isobutyl ketone, methyl-n-amyl ketone (2-heptanone), mesityl oxide, cyclopentanone and cyclohexanone. Examples of lactones include γ-butyrolactone and δ-lactone. Among these, δ-lactone is preferable.

Although there are no particular limitations on the amount of component (E) in the case of using component (E) in the composition for preparing emulsion or microemulsion formulations, the total amount of component (A), component (B) and component (C) is preferably 20% by weight to 50% by weight and more preferably 25% by weight to 40% by weight, the total amount of component (D) and component (E) is preferably 50% by weight to 80% by weight and more preferably 60% by weight to 75% by weight, and the amount of component (E) is preferably 10% by weight to 40% by weight and more preferably 15% by weight to 30% by weight, based on a value of 100% by weight for the total amount of component (A), component (B), component (C), component (D) and component (E).

In addition, the composition for preparing emulsion or microemulsion formulations according to the present invention may also contain an auxiliary component such as an ultraviolet absorber, an antioxidant, a preservative, an efficacy enhancer, a colorant or a fragrance within a range that does not impair the effects of the present invention. In addition, the composition for preparing emulsion or microemulsion formulations according to the present invention may also contain an agricultural chemical active ingredient (component (F)).

[Component (F)]

An agricultural chemical active ingredient may be used without any particular limitations provided that it is a compound used for the purpose of controlling pests. The agricultural chemical active ingredient used is not limited by whether it is a liquid or solid, whether it is an organic compound or inorganic compound, or whether it is a single compound or mixture. Examples of the agricultural chemical active ingredient include germicides, pest control agents (such as insecticides, miticides, nematicides and soil pesticides), herbicides, antifungal, anti-mold and anti-alga agents, plant growth regulators and rodent poisons.

Examples of germicides include: benzimidazole-based germicides such as benomyl, carbendazim, fuberidazole, thiabendazole or thiophanate methyl; dicarboxyimide-based germicides such as chlozolinate, iprodione, procymidone or vinclozolin; DMI germicides such as imzalil, oxpoconazole, pefurazoate, prochloraz, triflumizole, triforine, pyrifenox, fenarimol, nuarimol, azaconazole, bitertanol, bromconazole, cyproconazole, difenoconazole, diniconazole, epoxyconazole, fenbuconazole, fluquinconazole, flusilazole, flutriafol, hexaconazole, imibenconazole, ipuconazole, metconazole, myclobutanil, penconazole, propiconazole, prothioconazole, simeconazole, tebuconazole, tetraconazole, triadimefon, triadimenol, triticonazole, etaconazole, furconazole-cis, ipconazole or imibenconazole; phenylamide-based germicides such as benalaxyl, furalaxyl, metalaxyl, metalaxyl-M, oxadixyl or ofurace, amine-based germicides such as aldimorph, dodemorph, fenpropimorph, tridemorph, fenpropidine, piperalin or spiroxamine; phosphorothiolate-based germicides such as EDDP, iprobenfos or pyrazophos; dithiolane-based germicides such as isoprothiolane; carboxamide-based germicides such as benodanil, boscalid, carboxin, fenfuran, flutolanil, furametpyr, mepronil, oxycarboxin, penthiopyrad or thifluzamide; hydroxy(2-amino)pyrimidines such as bupirimate, dimethirimol or ethirimol; AP germicides (anilinopyrimidines) such as cyprodinil, mepanipyrim or pyrimethanil; N-phenylcarbamates such as diethofencarb; and, QoI germicides (Qo inhibitors) such as azoxystrobin, picoxystrobin, pyraclostrobin, kresoxim-methyl, trfloxystrobin, dimoxystrobin, metominostrobin, orysastrobin, famoxadone, fluoxastrobin, fenamidone or metominofen;

PP germicides (phenylpyrroles) such as fenpiconil or fludioxonil; quinoline-based germicides such as quinoxyfen; AH germicides (aromatic hydrocarbons) such as biphenyl, chloroneb, dichloran, quintozene, tecnazene or tolclofos-methyl; MRI-R germicides such as fthalide, pyroquilon or tricyclazole; MBI-D germicides such as carpropamid, diclocymet or fenoxanil; SBI agents such as fenhexamid, pyributicarb or terbinafine; phenylureas such as pencycuron; Qil germicides (Qi inhibitors) such as cyazofamid; benzamides such as zoxamide; enopyranurones such as blasticidin or mildiomycin; hexopyranosyls such as kasugamycin; giucopyranosyls such as streptomycin or validamycin; cyanoacetoamides such as cymoxanil; carbamates such as propamocarb, prothiocarb or polycarbamate; uncoupling agents such as binapacryl, dinocap, ferimzone or fluazinam; organic tin compounds such as triphenyltin acetate, triphenyltin chloride or triphenyltin hydroxide; phosphate esters such as phosphonic acid, tolclofos-methyl or fosetyl; phthalamides such as tecloftalam; benzotriazines such as triazoxide; benzene sulfonamides such as flusulfamide; pyridazinones such as diclomezine; CAA germicides (carbonic acid amides) such as dimethomorph, flumorph, benthiavalicarb, iprovalicarb or mandipropamide; tetracyclines such as oxytetracycline; thiocarbamates such as methasulfocarb; and, other compounds such as etridiazole, polyoxins, oxolinic acid, hydroxyisoxazole, octinoline, silthiofam, diflumetorim, acibenzolar-s-methyl, probenazole, tiadinil, ethaboxam, cyflufenamid, proquinazid, metrafenone, fluopicolide, cupric hydroxide, organic copper, sulfur, ferbam, manzeb, maneb, metiram, propineb, thiuram, zineb, ziram, captan, captafol, folpet, chlorothalonil, dichlofluanid, tolylfluanid, dodine, guazatine, iminoctadine acetate, iminoctadine dodecylbenzene sulfonate, anilazine, dithianon, chloropicrin, dazomet, metam sodium salt, chinomethionat, cyprofuram, silthiofam or fluoroimide.

Examples of insecticides, miticides, nematicides or soil pesticides, namely pest control agents, include:

organic (thio)phosphates such as acephate, azamethiphos, azinphos-methyl, chlorpyriphos, chlorpyriphos-methyl, chlorfenvinphos, diazinon, dichlorvos, dicrotophos, dimethoate, disulfoton, ethion, EPN, fenamiphos, fenitrothion, fenthion, isoxathion, malathion, methamidophos, methidathion, methyl parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprofos, tetrachlorvinphos, terbufos, triazophos, trichlorfon, fosthiazate, phosphocarb, cadusafos, disulfoton, demeton-s-methyl, BRP, CYAP, ethoprophos, quinalphos, dimethylvinphos, vamidothion or pyraclofos; carbamate-based agents such as alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, pyridafenthion, furathiocarb or XMC;

pyrethroids such as allethrin, bifenthrin, cyfluthrin, cyhalothrin, cyphenothrin, cypermethrin, alphacypermethrin, betacypermethrin, zetacypermethrin, deltamethrin, esfenvalerate, etofenprox, fenpropathrin, fenvalerate, imiprothrin, lambdacyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, acrinathrin, cycloprothrin, halfenprox or flucythrinate; chitin synthesis inhibitors such as chlorfluazuron, diflubenzuron, flucycloxuron, flufenoxuron, hexaflumuron, lufenuron, novaluron, teflubenzuron, triflumuron, bistrifluron, noviflumuron -buprofezin, diofenolan, hexythiazox, etoxazole or clofentazine, ecdysone antagonists such as halofenozide, methoxyfenozide, tebufenozide, chromafenozide or azadirachtin; juvenile hormone-like substances such as pyriproxyfen, methoprene or fenoxycarb; lipid biosynthesis inhibitors such as spirodiclofen, spiromesifen or spirotetramat;

nicotine receptor agonist/antagonist compounds such as acetamiprid, clothianidine, dinotefuran, imidacloprid, nitenpyram, thiacloprid or thiamethoxam; GABA antagonists such as acetoprole, endosulfan, ethiprole, fipronil, vaniliprole, pyrafluprole or pyriprole; macrocyclic lactone insecticides such as abamectin, emamectin, milbemectin, lepimectin, spinosad or ivermectin; METI I compounds such as fenazaquin, pyridaben, tebufenpyrad, tolfenpyrad or flufenerin; MET II and III compounds such as acequinocyl, fluacyprim or hydramethylnon; uncoupling agent compounds such as chlorfenapyr; oxidative phosphorylation inhibitor compounds such as cyhexatin, diafenthiuron, fenbutatin oxide or propargite; molting disruption compounds; mixed function oxidase inhibitor compounds such as piperonyl butoxide; sodium channel blocker compounds such as indoxacarb or metaflumizone; microbial pesticides such as BT agents, insect pathogen viral agents, insect pathogen fungal agents or nematode pathogen fungal agents; and other compounds such as benclothiaz, bifenazate, cartap, flonicamid, pyridalyl, pymetrozine, sulfur, thiocyclam, flubendiamide, cyenopyrafen, flupyrazofos, cyflumetofen, amidoflumet, bensultap, dicofol, tetradifon, fenpyroximate, amitraz, chlordimeform, triazamate, pymetrozine, pyrimidifen, 1,3-dichloropropene, clofentezine, fluacrypyrim, rotenone, DCIP, phenisobromolate, benzomate, methaldehyde, chlorantraniliprole spinetoram or pyrifluquinazon.

Examples of herbicides include 2,4-PA, ACN, CNP, DAP, DBN, DCBN, DCMU, DCPA, DPA, DSMA, IPC, MBPMC, MCC, MCP, MCPB, MCPP, MDBA, PAC, SAP, TCA, TCTP, ioxynil, asulam, atrazine, amiprofos-methyl, ametryn, alachlor, alloxydim, isouron, isoxaben, imazapyr, imazosulfuron, esprocarb, ethidimuron, oxadiazon, orthobencarb, karbutilate, quizalofop-ethyl, quinclorac, glyphosate, chlormethoxynil, clomeprop, chlorophthalim, cyanazine, dithiopyr, siduron, cinosulfuron, diphenamid, simazine, dimethametryn, simetryn, dimepiperate, terbacil, dymron, thiazafluron, thifensulfuron-methyl, tetrapion, thenylchlor, tebuthiuron, triclopyr, trifluralin, naproanilide, napropamide, bialaphos, picloram, bifenox, piperophos, Pyrazoxyfen, pyrazosulfuron-ethyl, pyrazolate, pyributicarb, phenoxaprop-ethyl, phenothiol, phenmedipham, butachlor, butamifos, flazasulfuron, fluazifop, pretilachlor, prodiamine, propyzamide, bromacil, prometryn, bromobutide, hexazinone, bethrodine, bensulfuron-methyl, benzofenap, bentazone, benthiocarb, pendimethalin, fosamine ammonium, methyl daimuron, metsulfuron-methyl, metolachlor, metribuzin, mefenacet, molinate, linuron or lenacil.

Examples of antifungal, anti-mold and anti-alga agents include tris-nitromethane, chlorobutanol, bronopol, glutaraldehyde, formaldehyde, α-bromocinnam aldehyde, 2-n-octyl-4-isothiazolin-3-one, 5-chloro-2-methyl-4-isothiazolin-3-one, 2-methyl-4-isothiazolin-3-one, 1,2-benzisothiazolin-3- one (BIT), 2-n-butyl-1,2-benzisothiazolin-3-one, allyl isothiocyanate, thiabendazole, methyl 2-benzimidazolylcarbamate, lauricidin, bioban, triclocarban, halocarban, glassy SiCAL, benzoic acid, sorbic acid, caprylic acid, propionic acid, 10-undecylenic acid, potassium sorbate, potassium benzoate, monomagnesium phthalate, 8-hydroxyquinoline, TMTD, triclosan, dichlohelanilide, trifluanid, milt protein, egg white lysozyme, benthiazole, carbam sodium, triazine, tebuconazole, hinokitiol, tetrachloroisophthalonitrile, 1,2-dibromo-2,4-dicyanobutane, chlorhexidine gluconate, polyhexamethylene biguanide, polyhexamethylene guanide, dantobrom, glydant, sodium pyrithion, zinc pyrithion, thymol, isopropyl methyl phenol, o-phenylphenol, phenol, butylparaben, ethylparaben, methylparaben, propylparaben, metacresol, ortho-cresol, para-cresol, sodium ortho-phenylphenol, chlorophene, parachlorphenol, parachloromethaxylate, parachlorocresol, fluorofolpet, polylysine, diiodomethyl para-tolyl sulfone, polyvinylpyrrolidone parachloroisocyanel, benzalkonium chloride, didecyldimethyl ammonium chloride, benzethonium chloride, cetyl ammonium bromide, cetrimide, CTAB, cetavlon, benzalkonium chloride, cetyl pyridinium chloride, DCMU, IPBC and TCMSP.

Examples of plant growth regulators include abscisic acid, indole butyric acid, uniconazole, ethychlozate, ethephon, cloxyfonac, chlormequat, chlorella extract, calcium peroxide, cyanamide, dichlorprop, gibberellin, daminozide, decyl alcohol, trinexapac-ethyl, mepiquat-chloride, paclobutrazol, paraffin, wax, piperonyl butoxide, pyraflufen ethyl, flurprimidol, prohydrojasmon, prohexadione-calcium, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene and aviglycine hydrochloride.

Examples of rodent poisons include coumarin-based rodent poisons and chlorophacinone.

Although there are no particular limitations on the amount of the agricultural chemical active ingredient (F), the component (F) may be preferably contained at 1 part by weight to 43 parts by weight and more preferably at 3 parts by weight to 25 parts by weight based on 100 parts by weight of the total amount of component (A), component (B), component (C), component (D) and component (E).

Although the composition for preparing emulsion or microemulsion formulations according to the present invention is normally a composition that does not contain water, water maybe contained as necessary. Although there are no particular limitations on the amount of water, an amount of water may be contained that dilutes a composition not containing water by 1.2 to 10 times.

Preparation of the composition for preparing emulsion or microemulsion formulations according to the present invention maybe carried out according to a known composition preparation method. For example, the composition may be prepared by mixing prescribed amounts of component (A), component (B), component (C), component (D) and, as necessary, component (E) followed by stirring. At that time, the order in which each component is added and mixed is arbitrary. A composition for preparing emulsion or microemulsion formulations obtained in such a manner is a composition that does not contain water, and can be stored, stocked or transported as is. Emulsion or microemulsion formulations can also be obtained by adding a prescribed amount of water and, as necessary, component (F) to the composition for preparing emulsion or microemulsion formulations not containing water.

In addition, preparation of a composition for preparing emulsion or microemulsion formulations containing water may be carried out by, for example, mixing prescribed amounts of component (A), component (B), component (C), component (D), water, and as necessary, component (E) followed by stirring. At that time, the order in which each component is added and mixed is arbitrary. Although there are no particular limitations on the amount of water, the amount of water may be that, for example, which dilutes the composition not containing water by 1.2 to 10 times. The composition containing water can be stored, stocked or transported as is. Although the composition containing water may be used as is as an emulsion or microemulsion formulation, a prescribed amount of component (F) and, as necessary, additional water can be added to the composition for preparing emulsion or microemulsion formulations containing water in anticipation of high agricultural chemical efficacy.

Moreover, preparation of a composition for preparing emulsion or microemulsion formulations containing an agricultural chemical active ingredient (component (F)) maybe carried out by, for example, mixing component (A), component (B), component (C), component (D), and as necessary, component (E) and/or water followed by stirring to obtain a composition, and then adding component (F) to the composition followed by stirring. In addition, this may also be carried out by mixing prescribed amounts of component (A), component (B), component (C), component (D), component (F), and as necessary, component (E) and/or water followed by stirring. At that time, the order in which each component is added and mixed is arbitrary. A composition for preparing emulsion or microemulsion formulations that contains an agricultural chemical active ingredient (component (F)) obtained in such a manner can be stored, stocked or transported as is. Although the composition containing water can also be used as is as an emulsion or microemulsion formulation containing component (F), it can also be diluted by further adding water as necessary.

EXAMPLES

The following provides a more detailed explanation of the present invention by indicating examples thereof. However, the present invention is not limited by the examples.

Example 1

28.7 parts by weight of 3-methoxy-3-methyl-1-butyl acetate (Solfit AC, Kuraray) were placed in a container equipped with a stirrer followed by the addition of 5.0 parts by weight of polyoxyethylene allyl phenyl ether (Newkalgen CP-15-200, Takemoto Oil & Fat), 5.0 parts by weight of polyoxyethylene sorbitan monooleate (Newkalgen D-945, Takemoto Oil & Fat), and 5.0 parts by weight of sodium dioctyl sulfosuccinate (Newkalgen EP-4C, Takemoto Oil & Fat) and dissolving by stirring. The mixture was suitably heated to promote dissolution.

The Newkalgen CP-15-200, Newkalgen D-945 and Newkalgen EP-4C were heated prior to use to remove any residual organic solvents and water.

2.1 parts by weight of acetamiprid (Nippon Soda), 2.1 parts by weight of propiconazole (Janssen Pharmaceutical) and 2.1 parts by weight of cyproconazole (Janssen Pharmaceutical) were added to the resulting solution followed by dissolving by stirring. 50.0 parts by weight of ion exchange water were gradually added thereto followed by stirring to obtain a composition for preparing a microemulsion formulation.

The composition was then diluted 100-fold with water to obtain a microemulsion formulation.

Example 2

30.0 parts by weight of 3-methoxy-3-methyl-1-butyl acetate (Solfit AC, Kuraray) and 10.0 parts by weight of y-butyrolactone were placed in a container equipped with a stirrer followed by the addition of 6.5 parts by weight of polyoxyethylene allyl phenyl ether (Newkalgen CP-15-200, Takemoto Oil & Fat), 6.5 parts by weight of polyoxyethylene sorbitan monooleate (Newkalgen D-945, Takemoto Oil & Fat), and 2.0 parts by weight of sodium dioctyl sulfosuccinate (Newkalgen EP-4C, Takemoto Oil & Fat) and dissolving by stirring. The mixture was suitably heated to promote dissolution.

The Newkalgen CP-15-200, Newkalgen D-945 and Newkalgen EP-4C were heated prior to use to remove any residual organic solvents and water.

2.1 parts by weight of acetamiprid and 2.1 parts by weight of cyproconazole were added to the resulting solution followed by dissolving by stirring. 20.0 parts by weight of a 50% aqueous solution of didecyl-dimethyl ammonium chloride (DDAC) (Sanyo Chemical Industries) and 22.8 parts by weight of ion exchange water were gradually added thereto followed by stirring to obtain a composition for preparing a microemulsion formulation.

The composition was then diluted 100-fold with water to obtain a microemulsion formulation.

Example 3

32.9 parts by weight of 3-methoxy-3-methyl-1-butyl acetate (Solfit AC, Kuraray), 6.0 parts by weight of polyoxyethylene ally phenyl ether (Newkalgen CP-15-200, Takemoto Oil & Fat), 6.0 parts by weight of polyoxyethylene sorbitan monooleate (Newkalgen D-945, Takemoto Oil & Fat), 3.0 parts by weight of sodium dioctyl sulfosuccinate (Newkalgen EP-4C, Takemoto Oil & Fat) and 2.1 parts by weight of n-butyl-BIT (Arch Chemicals Japan) were charged into a container equipped with a stirrer followed by dissolving by stirring. The mixture was suitably heated to promote dissolution.

The Newkalgen CP-15-200, Newkalgen D-945 and Newkalgen EP-4C were heated prior to use to remove any residual organic solvents and water.

50.0 parts by weight of ion exchange water were gradually added thereto followed by stirring to obtain a composition for preparing a microemulsion formulation.

The composition was then diluted 100-fold with water to obtain a microemulsion formulation.

The compositions for preparing a microemulsion formulation and the microemulsion formulations obtained in Examples 1 to 3 were allowed to stand at a temperature range of 0° C. to 40° C. The emulsions were maintained in a stable state even after the passage of one week.

Industrial Applicability

The composition for preparing emulsion or microemulsion formulations according to the present invention is able to provide emulsion or microemulsion formulations that demonstrate favorable dilution properties without being affected by the solubilities of constituent components. The composition for preparing emulsion or microemulsion formulations according to the present invention facilitates handling during preparation since it demonstrates little foaming. Moreover, the composition for preparing emulsion or microemulsion formulations according to the present invention enables the emulsion or microemulsion formulation to be maintained in a stable state even if diluted with water.

The invention claimed is:

1. A composition for preparing emulsion or microemulsion formulations comprising:
    a component (A): a polyoxyalkylene allyl phenyl ether, a polyoxyalkylene aralkyl phenyl ether or a polyoxyalkylene aralkenyl phenyl ether,
    a component (B): a polyoxyalkylene sorbitan alkylate,
    a component (C): a dialkylsulfosuccinate,
    a component (D): an ester ether-based solvent, and
    a component (E): a polar solvent other than the ester ether-based solvent, wherein the polar solvent other than the ester ether-based solvent is not water.

2. The composition for preparing emulsion or microemulsion formulations according to claim 1, wherein a ratio of a total amount of the component (A) and the component (B) to an amount of the component (C) is within a range of 1:2 to 1:7, and
    a ratio of an amount of the component (A) to an amount of the component (B) is within a range of 2:1 to 1:2.

3. The composition for preparing emulsion or microemulsion formulations according to claim 1, wherein a total amount of the component (A), the component (B) and the component (C) is 20% by weight to 50% by weight and an amount of the component (D) is 50% by weight to 80% by weight, based on a value of 100% by weight for a total amount of the component (A), the component (B), the component (C) and the component (D).

4. The composition for preparing emulsion or microemulsion formulations according to claim 1, wherein a total amount of the component (A), the component (B) and the component (C) is 20% by weight to 50% by weight, a total amount of the component (D) and the component (E) is 50% by weight to 80% by weight, and an amount of the component (E) is 10% by weight to 40% by weight, based on a value of 100% by weight for a total amount of component (A), component (B), component (C), component (D) and component (E).

5. The composition for preparing emulsion or microemulsion formulations according to claim 1, further comprising a component (F): an agricultural chemical active ingredient.

6. The composition for preparing emulsion or microemulsion formulations according to claim 5, comprising 1 to 43 parts by weight of the component (F) based on 100 parts by weight of a total amount of component (A), component (B), component (C), component (D) and component (E).

7. An emulsion or microemulsion formulation, comprising: the composition for preparing emulsion or microemulsion formulations according to claim 1.

8. An emulsion or microemulsion formulation obtained by diluting with water the composition for preparing emulsion or microemulsion formulations according to claim 1.

9. The emulsion or microemulsion formulation according to claim 7 or 8, which is used to preserve wood.

10. An emulsion or microemulsion formulation, comprising: the composition for preparing emulsion or microemulsion formulations according to claim 5.

11. The emulsion or microemulsion formulation according to claim 10, which is used to preserve wood.

12. An emulsion or microemulsion formulation obtained by diluting with water the composition for preparing emulsion or microemulsion formulations according to claim 5.

13. The emulsion or microemulsion formulation according to claim 12, which is used to preserve wood.

* * * * *